(12) United States Patent
Cote, Sr. et al.

(10) Patent No.: US 7,789,864 B2
(45) Date of Patent: Sep. 7, 2010

(54) LUER-ACTIVATED VALVE

(75) Inventors: Andrew L. Cote, Sr., Merrimack, NH (US); Charles F. Ganem, Cape Neddick, ME (US)

(73) Assignee: Nypro Inc., Clinton, MA (US)

( * ) Notice: Subject to any disclaimer, the term of this patent is extended or adjusted under 35 U.S.C. 154(b) by 0 days.

(21) Appl. No.: 10/700,344

(22) Filed: Nov. 3, 2003

(65) Prior Publication Data
US 2004/0138626 A1    Jul. 15, 2004

Related U.S. Application Data

(63) Continuation of application No. 09/810,087, filed on Mar. 16, 2001, now Pat. No. 7,100,890, which is a continuation of application No. 09/479,327, filed on Jan. 6, 2000, now Pat. No. 6,883,778, which is a continuation-in-part of application No. 09/394,169, filed on Sep. 13, 1999, now Pat. No. 6,039,302, which is a continuation of application No. 08/970,125, filed on Nov. 13, 1997, now abandoned.

(60) Provisional application No. 60/031,175, filed on Nov. 18, 1996, provisional application No. 60/034,708, filed on Jan. 3, 1997.

(51) Int. Cl.
*A61M 5/14* (2006.01)
(52) U.S. Cl. ..................... 604/256; 604/249
(58) Field of Classification Search ......... 604/244–256; 251/149.1
See application file for complete search history.

(56) References Cited

U.S. PATENT DOCUMENTS 2,594,405 A    4/1952   Deters .......................... 137/53
2,693,801 A    11/1954  Foreman ...................... 128/214
2,705,501 A    4/1955   Frizsch et al. ................ 137/113

(Continued)

FOREIGN PATENT DOCUMENTS

EP    0268480 A1    5/1988

(Continued)

OTHER PUBLICATIONS

U.S.P.T.O., Office Action dated Mar. 28, 2003, U.S. Appl. No. 09/808,418.

(Continued)

*Primary Examiner*—Kevin C Sirmons
*Assistant Examiner*—Elizabeth R Moulton
(74) *Attorney, Agent, or Firm*—Sunstein, Kann, Murphy & Timbers LLP

(57) ABSTRACT

A normally closed valve that may be opened upon insertion of a nozzle permits two-way flow when opened by a luer-taper nozzle. The valve also is able to resist large back pressures. The valve includes a substantially rigid housing that defines a passageway having an inlet section and an outlet section. The housing has an exterior inlet face to which the inlet section opens. The inlet section preferably has tapered and expanding zones. The tapered zone is adjacent to the exterior inlet face and is shaped to receive the nozzle. The expanding zone is adjacent to the tapered zone and has a larger inner diameter than the tapered zone's inner diameter. The exterior of the inlet section of the housing may have threads to accept luer-lock threads that may surround the nozzle.

41 Claims, 12 Drawing Sheets

U.S. PATENT DOCUMENTS

| | | | |
|---|---|---|---|
| 2,756,740 A | 7/1956 | Deane | 128/1 |
| 2,899,975 A | 8/1959 | Fernandez | 137/543.17 |
| 2,999,499 A | 9/1961 | Willett | 128/214 |
| 3,087,492 A | 4/1963 | Garth | 128/350 |
| 3,105,511 A | 10/1963 | Murphy, Jr. | 137/399 |
| 3,192,949 A | 7/1965 | De See | 137/540 |
| 3,385,301 A | 5/1968 | Harautuneian | 128/349 |
| 3,399,677 A | 9/1968 | Grould et al. | 128/349 |
| 3,416,567 A | 12/1968 | Von Dardel et al. | 137/604 |
| 3,506,005 A | 4/1970 | Gilio et al. | 128/214 |
| 3,538,950 A | 11/1970 | Porteners | 137/608 |
| 3,570,484 A | 3/1971 | Steer | 128/214 |
| 3,572,375 A | 3/1971 | Rosenberg | 137/512 |
| 3,726,282 A | 4/1973 | Patel | 128/349 BV |
| 3,806,086 A * | 4/1974 | Cloyd | 251/149.7 |
| 3,831,629 A | 8/1974 | Mackal et al. | 137/525 |
| 3,838,843 A * | 10/1974 | Bernhard | 251/149.1 |
| 3,923,065 A | 12/1975 | Nozick et al. | 128/348 |
| 3,965,910 A | 6/1976 | Fischer | 128/349 R |
| 3,994,293 A | 11/1976 | Ferro | 128/214 R |
| 4,041,432 A | 8/1977 | Yarworth et al. | 337/111 |
| 4,063,555 A | 12/1977 | Ulinder | 128/214 R |
| 4,080,965 A | 3/1978 | Phillips | 128/214 D |
| 4,094,195 A | 6/1978 | Friswell et al. | 73/422 GC |
| 4,094,196 A | 6/1978 | Friswell | 73/422 GC |
| 4,116,201 A | 9/1978 | Shah | 128/351 |
| 4,121,585 A | 10/1978 | Becker, Jr. | 128/214 R |
| 4,143,853 A | 3/1979 | Abramson | 251/149.1 |
| 4,223,808 A | 9/1980 | Williams et al. | 222/88 |
| 4,300,571 A | 11/1981 | Waldbillig | 128/673 |
| 4,324,239 A | 4/1982 | Gordon et al. | 128/214 R |
| 4,333,455 A | 6/1982 | Bodicky | 128/214.4 |
| 4,334,551 A | 6/1982 | Pfister | 137/614.03 |
| 4,344,435 A | 8/1982 | Aubin | 128/350 R |
| 4,387,879 A | 6/1983 | Tauschinski | 251/149.1 |
| 4,401,432 A | 8/1983 | Schwartz | 604/89 |
| 4,421,296 A | 12/1983 | Stephens | 251/149.7 |
| 4,429,856 A | 2/1984 | Jackson | 251/149.1 |
| 4,458,480 A | 7/1984 | Irwin | 60/39.63 |
| 4,496,348 A | 1/1985 | Genese et al. | 604/167 |
| 4,498,658 A | 2/1985 | Mikiya | 251/149.6 |
| 4,534,758 A | 8/1985 | Akers et al. | 604/85 |
| 4,535,820 A | 8/1985 | Raines | 137/854 |
| 4,550,785 A | 11/1985 | Hibbard et al. | 173/134 |
| 4,551,136 A | 11/1985 | Mandl | 604/141 |
| 4,585,435 A | 4/1986 | Vaillancourt | 604/27 |
| 4,596,557 A | 6/1986 | Pexa | 604/86 |
| 4,611,973 A | 9/1986 | Birdwell | 417/342 |
| 4,617,015 A | 10/1986 | Foltz | 604/100 |
| 4,661,110 A | 4/1987 | Fortier et al. | 604/256 |
| 4,675,003 A | 6/1987 | Hooven | 604/9 |
| 4,681,132 A | 7/1987 | Lardner | 137/271 |
| 4,683,905 A | 8/1987 | Vigneau et al. | 137/329 |
| 4,683,916 A | 8/1987 | Raines | 137/854 |
| 4,698,061 A | 10/1987 | Makaryk et al. | 604/408 |
| 4,710,168 A | 12/1987 | Schwab et al. | 604/99 |
| 4,712,583 A | 12/1987 | Pelmulder et al. | 137/852 |
| 4,743,235 A | 5/1988 | Waldbillig et al. | 604/250 |
| 4,745,950 A | 5/1988 | Mathieu | 137/798 |
| 4,749,003 A | 6/1988 | Leason | 137/854 |
| 4,752,287 A | 6/1988 | Kurtz et al. | 604/99 |
| 4,752,292 A | 6/1988 | Lopez et al. | 604/244 |
| 4,758,224 A | 7/1988 | Siposs | 604/119 |
| 4,776,369 A | 10/1988 | Lardner et al. | 137/515.5 |
| 4,809,679 A | 3/1989 | Shimonaka et al. | 128/4 |
| 4,816,020 A | 3/1989 | Brownell | 604/97 |
| 4,819,684 A | 4/1989 | Zaugg et al. | 137/112 |
| 4,850,978 A | 7/1989 | Dudar et al. | 604/201 |
| 4,874,377 A | 10/1989 | Newgard et al. | 604/167 |
| 4,915,687 A | 4/1990 | Sivert | 604/83 |
| 4,917,668 A | 4/1990 | Haindl | 604/167 |
| 4,935,010 A | 6/1990 | Cox et al. | 604/122 |
| 4,966,199 A | 10/1990 | Ruschke | 137/843 |
| 5,006,114 A | 4/1991 | Rogers et al. | 604/167 |
| 5,041,087 A | 8/1991 | Loo et al. | 604/83 |
| 5,048,537 A | 9/1991 | Messinger | 128/673 |
| 5,049,128 A | 9/1991 | Duquette | 604/83 |
| 5,059,175 A | 10/1991 | Hanover et al. | 604/891.1 |
| 5,065,783 A | 11/1991 | Ogle, II | 137/68.1 |
| 5,080,654 A | 1/1992 | Picha et al. | 604/167 |
| 5,085,645 A | 2/1992 | Purdy et al. | 604/167 |
| 5,100,394 A | 3/1992 | Dudar et al. | 604/283 |
| 5,108,380 A | 4/1992 | Herlitze et al. | 604/283 |
| 5,122,123 A | 6/1992 | Vaillancourt | 604/192 |
| 5,127,904 A | 7/1992 | Loo et al. | 604/83 |
| 5,147,333 A | 9/1992 | Raines | 604/249 |
| 5,171,230 A | 12/1992 | Eland et al. | 604/250 |
| 5,184,652 A | 2/1993 | Fan | 141/21 |
| 5,190,067 A * | 3/1993 | Paradis et al. | 137/1 |
| 5,199,947 A | 4/1993 | Lopez et al. | 604/56 |
| 5,201,715 A | 4/1993 | Masters | 604/175 |
| 5,203,775 A | 4/1993 | Frank et al. | 604/256 |
| 5,215,538 A | 6/1993 | Larkin | 604/249 |
| 5,221,271 A | 6/1993 | Nicholson et al. | 604/283 |
| 5,230,706 A | 7/1993 | Duquette | 604/83 |
| 5,242,393 A | 9/1993 | Brimhall et al. | 604/86 |
| 5,242,432 A | 9/1993 | DeFrank | 604/284 |
| 5,269,771 A | 12/1993 | Thomas et al. | 604/213 |
| 5,280,876 A | 1/1994 | Atkins | 251/149.1 |
| 5,300,034 A | 4/1994 | Behnke et al. | 604/167 |
| 5,320,328 A | 6/1994 | Decloux et al. | 251/326 |
| 5,330,435 A | 7/1994 | Vaillancourt | 604/167 |
| 5,349,984 A | 9/1994 | Weinheimer et al. | 137/543.21 |
| 5,360,413 A * | 11/1994 | Leason et al. | 604/249 |
| 5,380,306 A | 1/1995 | Brinon | 604/244 |
| 5,390,898 A | 2/1995 | Smedley et al. | 251/149.6 |
| 5,401,255 A | 3/1995 | Sutherland et al. | 604/247 |
| 5,439,451 A * | 8/1995 | Collinson et al. | 604/247 |
| 5,441,487 A | 8/1995 | Vedder | 604/167 |
| 5,458,640 A | 10/1995 | Gerrone | 604/264 |
| 5,465,938 A * | 11/1995 | Werge et al. | 251/149.1 |
| 5,474,536 A | 12/1995 | Bonaldo | 604/86 |
| 5,474,544 A | 12/1995 | Lynn | 604/283 |
| 5,509,433 A | 4/1996 | Paradis | 137/1 |
| 5,509,912 A | 4/1996 | Vaillancourt et al. | 604/283 |
| 5,520,665 A | 5/1996 | Fleetwood | 604/283 |
| 5,520,666 A | 5/1996 | Choudhury et al. | 604/283 |
| 5,533,708 A | 7/1996 | Atkinson et al. | 251/149.1 |
| 5,533,983 A | 7/1996 | Haining | 604/249 |
| 5,540,661 A | 7/1996 | Tomisaka et al. | 604/265 |
| 5,549,566 A | 8/1996 | Elias et al. | 604/167 |
| 5,549,577 A | 8/1996 | Siegel et al. | 604/256 |
| 5,555,908 A | 9/1996 | Edwards et al. | 137/329.1 |
| 5,569,209 A | 10/1996 | Roitman | 604/190 |
| 5,569,235 A * | 10/1996 | Ross et al. | 604/403 |
| 5,573,516 A | 11/1996 | Tyner | 604/249 |
| 5,578,059 A * | 11/1996 | Patzer | 604/249 |
| 5,613,663 A | 3/1997 | Schmidt et al. | 251/149.2 |
| 5,616,129 A | 4/1997 | Mayer | 604/167 |
| 5,616,130 A | 4/1997 | Mayer | 604/167 |
| 5,620,434 A * | 4/1997 | Brony | 604/406 |
| 5,674,206 A | 10/1997 | Allton et al. | 604/249 |
| 5,676,346 A | 10/1997 | Leinsing | 251/149.1 |
| 5,685,842 A | 11/1997 | Drivas | 604/49 |
| 5,685,866 A | 11/1997 | Lopez | 604/249 |
| 5,694,686 A | 12/1997 | Lopez | 29/890.126 |
| 5,695,466 A | 12/1997 | Lopez et al. | 604/93 |
| 5,699,821 A | 12/1997 | Paradis | 137/1 |
| 5,700,248 A * | 12/1997 | Lopez | 604/249 |
| 5,730,418 A | 3/1998 | Feith et al. | 251/149.6 |
| 5,749,861 A | 5/1998 | Guala et al. | 604/249 |
| RE35,841 E | 7/1998 | Frank et al. | 604/256 |
| 5,788,215 A | 8/1998 | Ryan | 251/149.6 |
| 5,806,831 A | 9/1998 | Paradis | 251/149.1 |

| | | | |
|---|---|---|---|
| 5,817,069 A | 10/1998 | Arnett | 604/256 |
| 5,820,601 A | 10/1998 | Mayer | 604/167 |
| 5,921,264 A | 7/1999 | Paradis | 137/15 |
| 5,954,313 A | 9/1999 | Ryan | 251/149.1 |
| 6,029,946 A | 2/2000 | Doyle | 251/149.1 |
| 6,036,171 A | 3/2000 | Weinheimer et al. | 251/149.1 |
| 6,039,302 A * | 3/2000 | Cote et al. | 251/149.1 |
| 6,048,335 A | 4/2000 | Mayer | 604/167 |
| 6,050,978 A | 4/2000 | Orr et al. | 604/249 |
| 6,063,062 A | 5/2000 | Paradis | 604/249 |
| 6,068,011 A | 5/2000 | Paradis | 137/1 |
| 6,079,432 A * | 6/2000 | Paradis | 137/1 |
| 6,089,541 A | 7/2000 | Weinheimer et al. | 251/149.6 |
| 6,142,446 A | 11/2000 | Leinsing | 251/149.1 |
| 6,152,900 A | 11/2000 | Mayer | 604/167 |
| 6,158,458 A | 12/2000 | Ryan | 137/515.5 |
| 6,189,859 B1 | 2/2001 | Rohrbough et al. | 251/149.1 |
| 6,206,860 B1 | 3/2001 | Richmond | 604/246 |
| 6,228,069 B1 | 5/2001 | Barth et al. | 604/249 |
| 6,245,048 B1 | 6/2001 | Fangrow, Jr. et al. | 604/249 |
| 6,290,206 B1 | 9/2001 | Doyle | 251/149.1 |
| 6,344,033 B1 | 2/2002 | Jepson et al. | 604/256 |
| 6,428,520 B1 | 8/2002 | Lopez et al. | 604/249 |
| 6,485,472 B1 | 11/2002 | Richmond | 604/246 |
| 6,543,745 B1 | 4/2003 | Enerson | 251/149.7 |
| 6,585,229 B2 | 7/2003 | Cote, Sr. et al. | 251/149.1 |
| 6,595,964 B2 | 7/2003 | Finley et al. | 604/246 |
| 6,609,696 B2 | 8/2003 | Enerson | 251/86 |
| 6,669,673 B2 | 12/2003 | Lopez | 604/249 |
| 6,755,391 B2 * | 6/2004 | Newton et al. | 251/149.6 |
| 6,883,778 B1 | 4/2005 | Newton et al. | 251/149.1 |
| 7,100,890 B2 | 9/2006 | Cote, Sr. et al. | 251/149.1 |
| 2002/0002351 A1* | 1/2002 | Cote et al. | 604/247 |
| 2002/0024036 A1 | 2/2002 | Rohrbough et al. | 251/149.1 |
| 2003/0050610 A1 | 3/2003 | Newton et al. | 604/256 |
| 2003/0060779 A1 | 3/2003 | Richmond | 604/256 |
| 2003/0093061 A1 | 5/2003 | Ganem | 604/533 |
| 2003/0098430 A1 | 5/2003 | Leinsing et al. | 251/149.6 |
| 2003/0141477 A1 | 7/2003 | Miller | 251/149.1 |
| 2004/0073171 A1 | 4/2004 | Rogers et al. | 604/164.13 |

FOREIGN PATENT DOCUMENTS

| | | |
|---|---|---|
| EP | 0629418 A1 | 12/1994 |
| EP | 1243285 | 9/2002 |
| GB | 2 079 162 | 1/1982 |
| GB | 01/20218 A1 | 3/2001 |
| WO | 83/02559 | 8/1983 |
| WO | 93/11828 | 6/1993 |
| WO | 96/00107 | 1/1996 |
| WO | 97/39791 | 10/1997 |
| WO | 98/22178 | 5/1998 |
| WO | 98/26835 | 6/1998 |
| WO | 98/39594 | 9/1998 |
| WO | 00/44433 | 8/2000 |
| WO | WO 03/018104 A2 | 3/2003 |
| WO | WO 03/018105 A1 | 3/2003 |
| WO | WO 2004/060466 | 7/2004 |

OTHER PUBLICATIONS

U.S.P.T.O., Office Action dated Sep. 6, 2007, U.S. Appl. No. 09/808,418.

U.S.P.T.O., Office Action dated Feb. 14, 2008, U.S. Appl. No. 09/808,418.

Bromberg & Sunstein LLP, Response to Office Action dated Mar. 28, 2003, U.S. Appl. No. 09/808,418.

* cited by examiner

LUER-ACTIVATED VALVE

PRIORITY

This patent application is a continuation of U.S. patent application Ser. No. 09/810,087, filed Mar. 16, 2001 now U.S. Pat. No. 7,100,890. U.S. patent application Ser. No. 09/810,087 is a continuation of U.S. patent application Ser. No. 09/479,327, filed Jan. 6, 2000 now U.S. Pat. No. 6,883,778, (which is a non-provisional of U.S. Provisional Patent Application No. 60/117,359), which is a continuation-in-part of U.S. patent application Ser. No. 09/394,169, filed Sep. 13, 1999 now U.S. Pat. No. 6,039,302, which is a continuation of U.S. patent application Ser. No. 08/970,125, filed Nov. 13, 1997 now abandoned, which is a non-provisional of U.S. Provisional Patent Application No. 60/031,175, filed Nov. 18, 1996, and U.S. Provisional Patent Application No. 60/034,708, filed Jan. 3, 1997. All of these patents and patent applications are incorporated herein, in their entireties, by reference.

TECHNICAL FIELD

The present invention relates to valves that may be actuated by nozzles and in particular by male Luer fittings.

SUMMARY OF THE INVENTION

The present invention is directed to a normally closed valve that may be opened upon insertion of a nozzle, which in a preferred embodiment is a male Luer fitting. The valve permits two-way flow when opened by a luer-taper nozzle and is able to resist large back pressures. The valve includes a substantially rigid housing that defines a passageway having an inlet section and an outlet section. The housing has an exterior inlet face to which the inlet section opens. The inlet section preferably has tapered and expanding zones, with the tapered zone being adjacent the exterior inlet face and being shaped to receive the nozzle, and with the expanding zone being adjacent to the tapered zone and having a larger inner diameter than the tapered zone's inner diameter. Preferably, the exterior of the inlet section of the housing has threads to accept luer-lock threads that may surround the nozzle.

The valve also includes a substantially rigid cannula disposed within the passageway and extending into the inlet section. The cannula is movable between first and second positions corresponding to closed and open modes of the valve. The valve further includes a substantially flexible, resilient gland member having (i) a seal section disposed over the inlet end of the cannula, (ii) a tubular section connected to the seal section and disposed around the cannula between cannula and the housing, and in a preferred embodiment, (iii) an attachment section connected to the tubular section and attached to the housing. The seal section has a normally closed aperture therethrough, and preferably has an outer diameter that is larger than the inner diameter of the tapered zone of the housing's inlet section and smaller than the inner diameter of the expanding zone.

The inlet end of the cannula and the gland are preferably shaped so as to permit the gland's seal section to move with respect to the cannula. Preferably, the valve includes means for limiting this movement of the seal section, for example by including a step on either the cannula's inlet end or the inner diameter of the gland. The inlet end of the cannula may be shaped to urge the seal section open when nozzle presses the seal section against the inlet end of the cannula while the seal section is in the expanding zone of the housing inlet section.

In a preferred embodiment, a space is provided between the seal section and the cannula when the valve is in the closed position.

When the valve is in its closed mode, the seal section is substantially aligned with the exterior inlet face of the housing so as to provide a swabbable surface; preferably the seal section extends a small amount beyond the exterior inlet face so as to ensure that the seal section surface is fully swabbable. Preferably, the outlet end of the cannula is shaped so as to provide a back-pressure seal with the attachment section of the gland member.

In a preferred embodiment, the attachment section of the gland member is stretched as the valve is urged by the nozzle from the valve's closed mode to the valve's opened mode. In addition, the tubular section of the gland member is preferably compressed as the valve is urged by the nozzle from the valve's closed mode to the valve's opened mode. In an alternative embodiment, the outlet end of the cannula is shaped (e.g., as a leaf spring) to provide a flexible member that urges the cannula into the first position.

The housing preferably includes gland-stopping structure for stopping movement of the gland towards the outlet section of the valve independently of movement of the cannula. Cannula-stopping structure may also be provided, on the housing or on the cannula's outlet end, for stopping movement of the cannula towards the outlet section of the valve while permitting flow to the outlet section of the valve.

These and other features, aspects and advantages of the present invention will become better understood with regard to the following description taken in conjunction with the accompanying drawings wherein are set forth, by way of illustration and example, certain embodiments of this invention.

DETAILED DESCRIPTION OF SPECIFIC EMBODIMENTS

Figure 1:
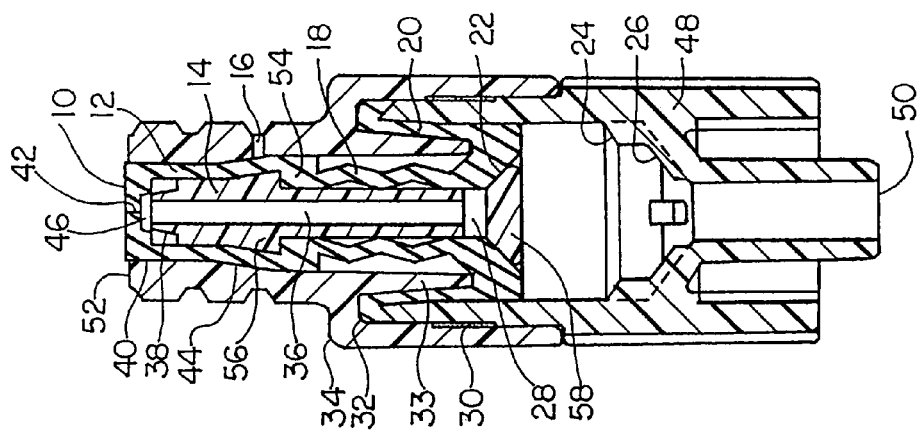
FIG. 1 shows a longitudinal sectional view of a valve according to one embodiment of the invention.
Figure 6:
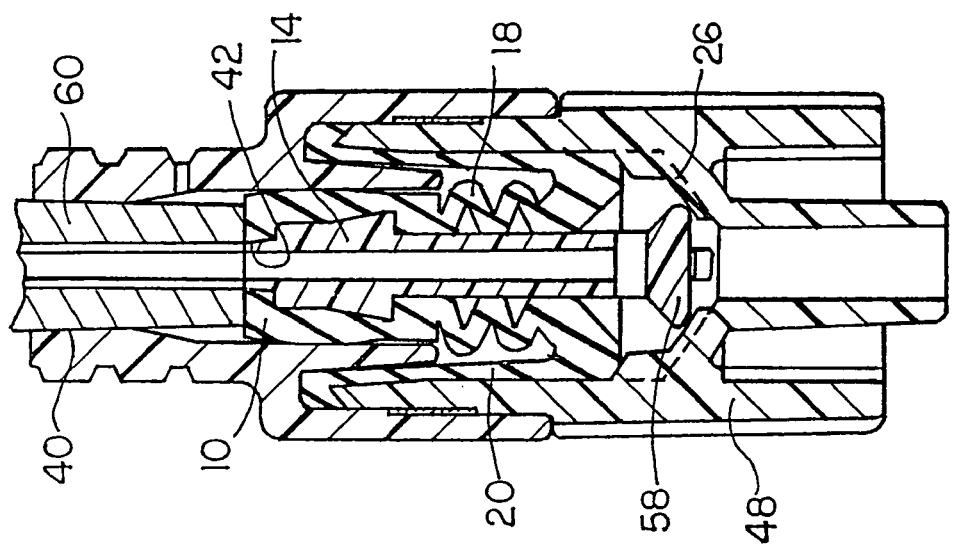

As shown in FIG. 1, in a preferred embodiment of the invention, the valve is made from four components: an inlet housing portion 34, an outlet housing portion 48, a gland 12 and a movable, rigid interior cannula 14. The two housing portions preferably are ultrasonically shear welded together at area 30, so as to form an integral housing and so as to hold one end of the gland 12 in a gland-retention area 32. Fluid passing through the valve passes through the cannula 14, which is located within the gland 12, which in turn is located within the housing.

The gland 12 has three sections: a swabbable seal section 10, a tubular section 18 and an attachment section 20. Preferably, the valve is made from silicone. The seal section 10 has an aperture 42 passing through it; the aperture 42 may be, for example, a pierced hole or a slit. When the valve is in the closed mode, as shown in FIG. 1, the aperture 42 is held closed by the inner surface of the housing; the inner diameter of the housing at the inlet is smaller than the outer diameter of the seal section 10 of the gland 12, so that the housing squeezes the seal section 12, thereby forcing the aperture 42 closed. This compression zone 40 of the passageway through the housing is tapered to accept and hold a luer-tapered nozzle (item 60 in FIG. 2). Further down the housing's passageway a second zone 44 has an inner diameter that is greater than that of the tapered, compression zone 40 and greater than the outer diameter of the seal section 10, so that the seal section may expand when it is forced into this zone, thereby permitting the aperture 42 to open. The inlet housing portion 34 preferably includes a vent 16 to ease the movement of the seal section 10 between the expanding zone and the tapered zone. When the valve is in the fully closed position, the gland's seal section 10 is flush with or extends slightly above the exterior inlet face 52 of the housing. The seal section 10 and the exterior inlet face 52 thus present a swabbable surface, i.e., they may be easily wiped clean with an alcohol swab, for instance.

The tubular section 18 of the gland 12 is preferably designed to be compressible. Another section 54 of the gland 12, located between the seal section and the compressible, tubular section may be shaped to match a corresponding ledge 56 on the cannula 14, so as to hold the top section of the gland 12 in place on the cannula.

In addition to the seal section 10 of the gland 12, the valve has a second seal area 22 at the outlet end of the cannula 14. The outlet end 58 of the cannula 14 is shaped so as to provide a seal against the gland 12. The cannula's outlet end 58 has a wider outer diameter than the inner diameter of the compressible, tubular section 18 of the gland, and the fluid passageway 36 through the cannula has a channel 28 that redirects the passageway sideways into the gland 12. This arrangement forms a seal when the valve is in the closed position, as shown in FIG. 1, and is able to resist a large amount of back pressure from the outlet end 50 of the valve. The inlet housing portion 34 preferably includes a rigid annular extension 33 that separates the gland's tubular section 18 from the gland's attachment section 20. This annular extension 33 ensures that the tubular and attachment sections of the gland 12 do not fold incorrectly when the valve is opened and closed. In addition, the annular extension 33, in connection with the gland, ensures that the cannula's outlet section 58 does not get forced too far up into the inlet section by a large amount of back pressure. The annular extension 33 also prevents the lower portion of the gland 12 from being forced too far up into the inlet section. Since the valve has a second seal area 22, formed by the cannula's outlet end 58, that is able to resist large back pressures, the first seal—the aperture 42 through the gland's seal section 10—does not have to resist large back pressures.

Preferably, the gland's tubular section 18 is preloaded, by making the gland's tubular section sufficiently long with respect to the distance between the cannula's ledge 56 and the cannula's outlet end 58, so that the gland's tubular section is under compression even when the valve is in the closed position. This arrangement improves the effectiveness of the second seal area 22. By preloading the gland's tubular section 18, the valve is made more resistant to opening in response to either a positive pressure or a negative pressure applied to the outlet 50. By having a sufficient amount of surface area of the gland 12 exposed to the outlet 50 with respect to the surface area of the cannula 14 exposed to the outlet, the effect on a closed valve of a negative pressure at the outlet will be to pull the gland toward the outlet along with the cannula 14. By having a negative pressure pull both the gland 12 and the cannula 14 toward the outlet, the second seal area 22 remains sealed.

The cannula's outlet end 58 may be made thin, so that in an emergency a needle—instead of a luer-taper nozzle—may be used with the valve. The needle may be inserted through the seal section's aperture 42 through the cannula's passageway, and then, if the outlet end 58 is made thin enough, the needle may pierce the outlet so that medication may be injected through the valve. The outlet end does need to be strong enough to resist whatever level of back pressure may be expected from the valve's outlet 50.

The outlet housing portion 48 includes a ledge 24 to prevent the gland 12—in particular, the gland's attachment section 20—from extending too far towards the valve's outlet 50. This ledge 24 does not stop the movement of the cannula 14 towards the outlet 50; thus, the cannula's outlet end 58 may continue to move toward the valve's outlet 50 and separate from the gland 12, thereby opening the second seal area 22, if it has not yet opened. The outlet housing portion 48 also includes ribs 26 for stopping the movement of the cannula 14 toward the valve's outlet 50, while permitting flow from the cannula 14 between the ribs 26 to the valve's outlet.

Figure 2:
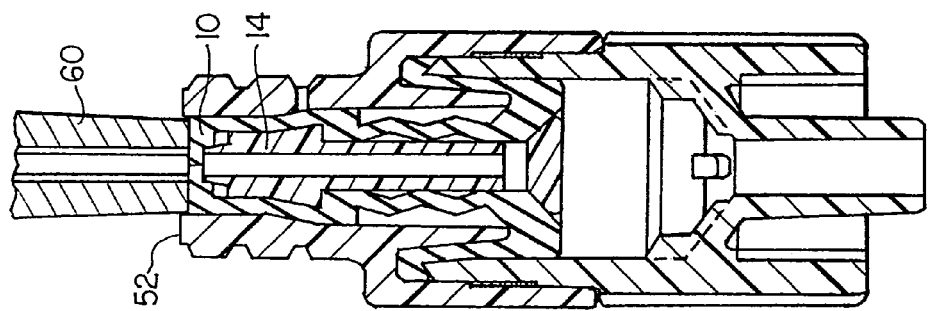

To facilitate the centering of the nozzle as it is being inserted into the valve, the interior surface of the gland's seal section 10 has a small hollow area 46 shaped to receive the inlet end 38 of the cannula 14. The inlet end of the cannula 14 is shaped to cause the opening of the seal section's aperture 42 when the seal section 10 is squeezed between the cannula 14 and the nozzle with sufficient force. When the nozzle 60 is first pressed against the gland's seal section 10, the seal section 10 is pressed toward the cannula 14, causing the hollow area 46 of the seal section 10 down over the inlet end 38 of the cannula 14, as shown in FIG. 2. This motion causes the top of the inlet section 10 to fall below the exterior inlet face 52 of the housing, thereby facilitating the centering of the nozzle 60.

Figure 3:
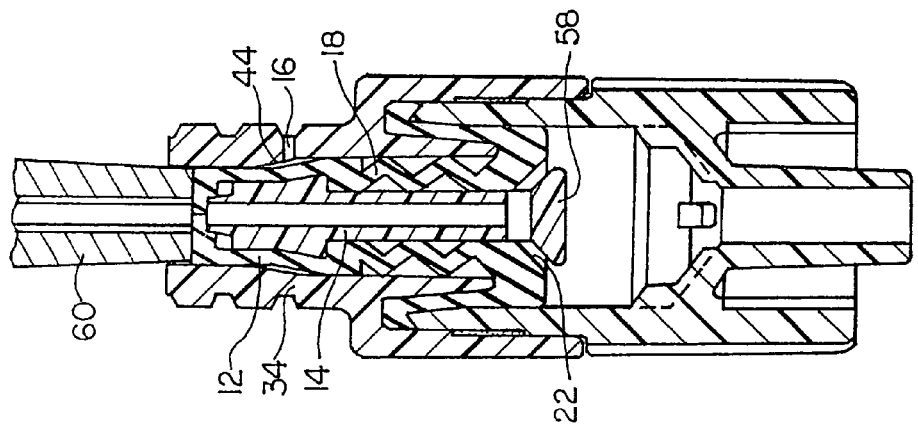
FIGS. 2-6 show longitudinal sectional views of the valve shown in FIG. 1, as the valve is urged by a luer-taper nozzle from a fully closed position to a fully open position.
Figure 4:
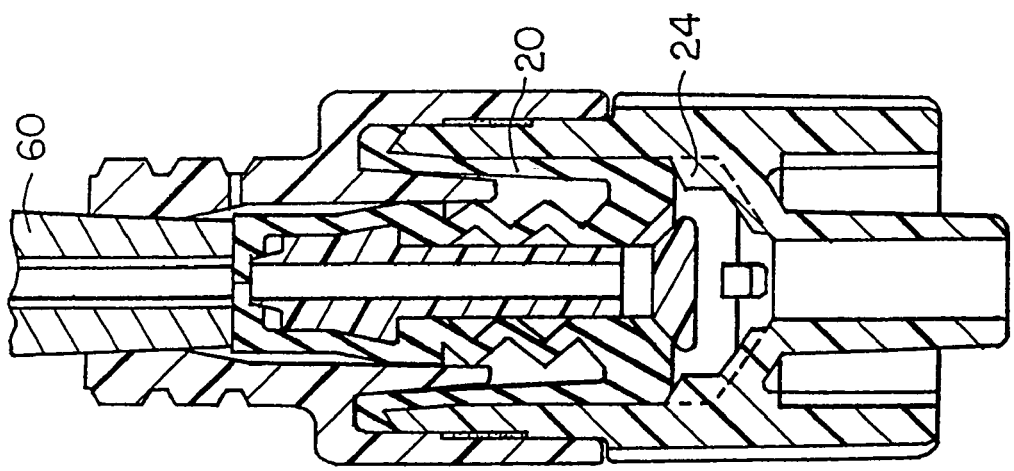

As can be seen in FIG. 3, as the nozzle 60 is continued to be pushed into the valve, the vent 16 allows the gland 12 to separate from the expanding zone 44 of the inlet housing portion 34, thereby easing the movement of the gland 12 through the inlet housing portion 34. At some point as the cannula 14 is forced down into the valve, the cannula's outlet end 58 separates from the gland 12, thereby opening up the second seal area 22. This opening of the second seal area occurs as the compressible, tubular section 18 of the gland 12 is compressed by the nozzle 60 pushing the cannula 14 downward. As shown in FIG. 4, further insertion of the nozzle 60 into the valve results in the attachment section 20 of the gland stretching until it reaches the ledge 24, which prevents further stretching of the attachment section 20.

Figure 5:
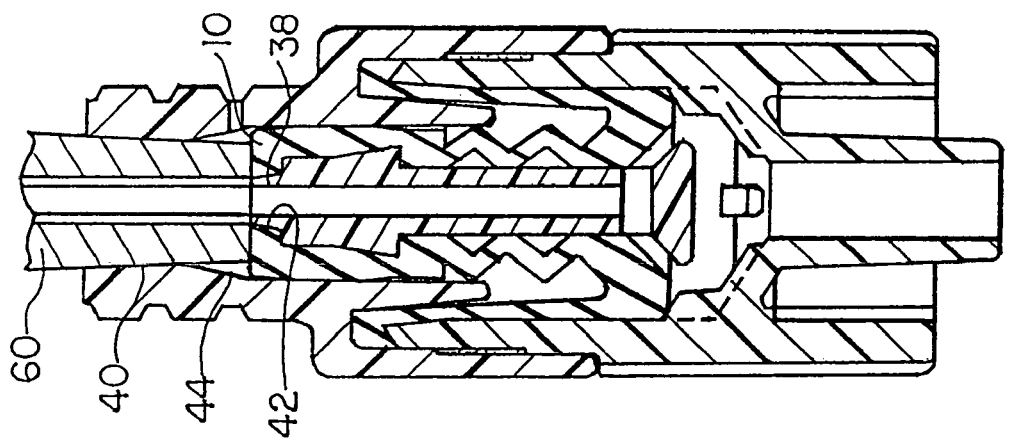

FIG. 5 shows the nozzle 60 and the cannula's inlet end 38 having forced open the aperture 42 in the gland's seal section 10. Because the seal section 10 is in the widened zone 44 of the housing's passageway, the seal section 10 has room to spread. After the seal section's aperture 42 is opened, the luer-taper nozzle 60 should become fully seated in the tapered zone 40 of the inlet. If the nozzle 60 forces the cannula 14 too far down, movement of the cannula 14 will be stopped by ribs 26. The ribs 26 permit flow between the cannula's outlet end and the outlet housing portion 48, even when the cannula 14 is pushed down all the way. After the nozzle is removed from the valve, the stretched attachment section 20 of the gland and the compressed tubular section of the gland 18 tend to return to their original shapes, causing the seal section 10 to be forced back into the tapered zone 40. Since, as noted above, the tapered zone 40 has a smaller diameter than the outer diameter of the seal section 10, the aperture 42 is squeezed closed, thereby returning the valve to its closed mode.

Figure 8:
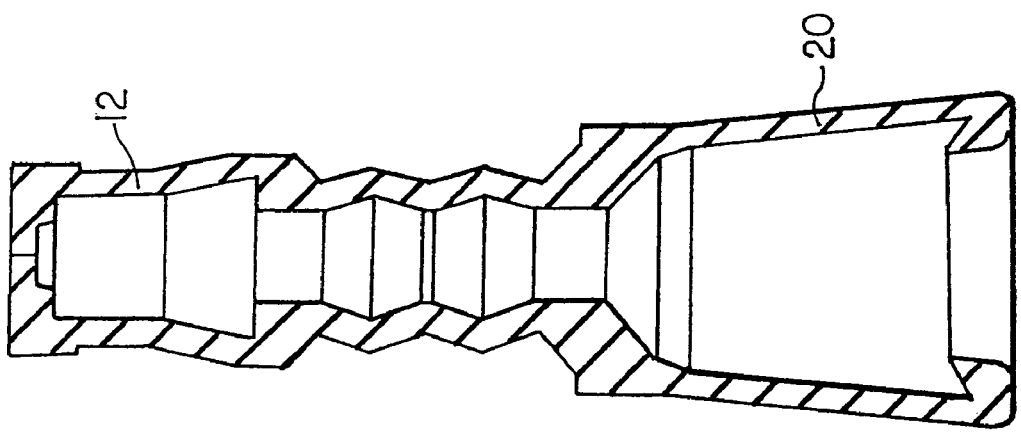
Figure 7:
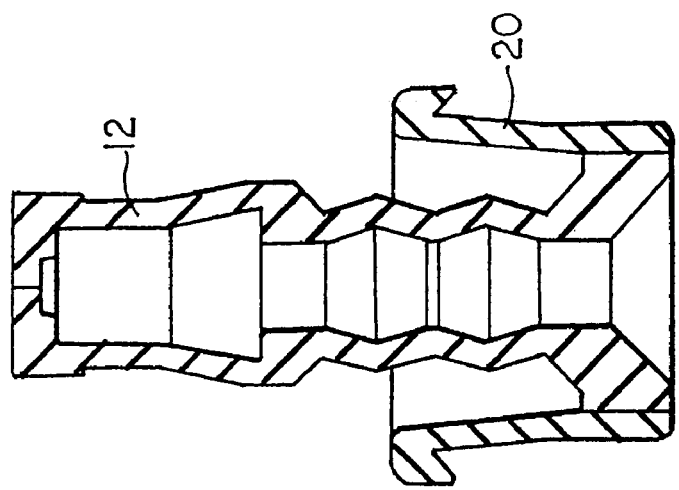

FIG. 7 shows an alternative embodiment for the gland 20 shown in FIG. 1. The FIG. 7 gland is molded in two shots, so that the attachment section 20 is made of a type of silicone or other material that has good stretching properties, while the rest of the gland is made of material that has good compression properties. FIG. 8 shows a gland 12 made according to a method that simplifies molding considerations. The gland 12 is molded in the shape shown in FIG. 8, which shape is simpler to mold than the gland shape shown in FIGS. 1 and 7; the attachment section 20 is folded upward prior to it being attached to the gland retention area (item 32 in FIG. 1) between the inlet housing portion 34 and the outlet housing portion 48 during ultrasonic welding.

Figure 9:
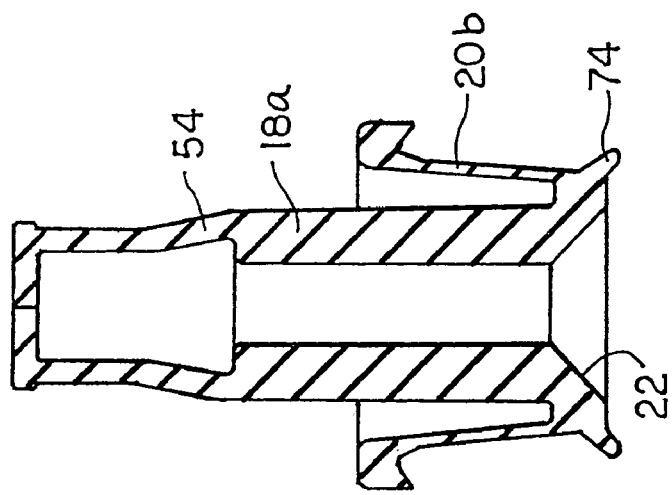
FIGS. 7-9 show longitudinal section views of three alternative embodiments of the gland that may be used in the valve shown in FIG. 1.

FIG. 9 shows a preferred embodiment of the gland that may be used in the FIG. 1 valve. The tubular section 18a of the gland, instead of being accordion-shaped like the gland shown in FIG. 1, has a simple annular design. When the valve is assembled, this tubular section 18a is preferably preloaded in a compressed state when the valve is closed in order to maintain sufficient sealing force at the seal area against the outlet end of the cannula 14. As noted above, such preloading may be accomplished by making the tubular section 18a between the seal area 22 and the section 54 of the gland that corresponds to the ledge on the cannula longer than the corresponding section on the cannula 14.

In order to reduce friction between the housing and the attachment section 20b of the gland, the contact between the attachment section and the housing may be limited to a wiper member 74. The wiper member 74 helps ensure that liquid does not make its way up into the section between the attachment section 20b and the housing, while reducing the contact area between the attachment section 20b and the housing. In such an embodiment, the attachment section 20b may include a vent port therethrough in order to prevent a vacuum forming between the attachment section and the housing.

Figure 11:
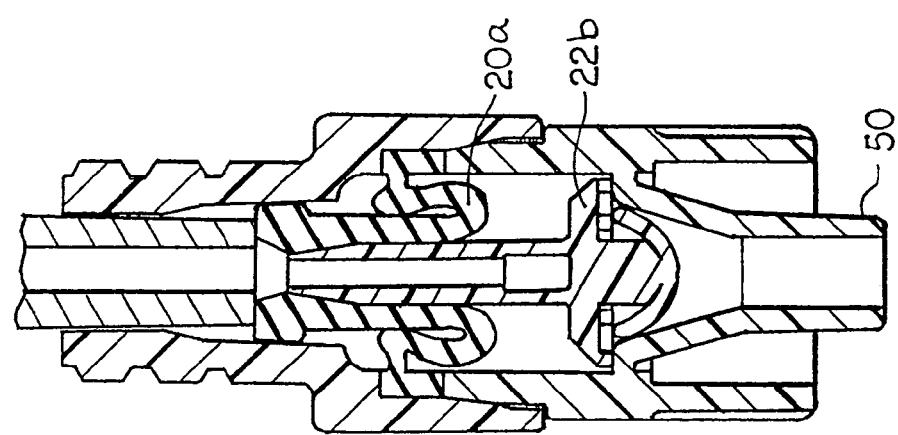
FIG. 11 shows a variation of the FIG. 10 embodiment in the open position.
Figure 10:
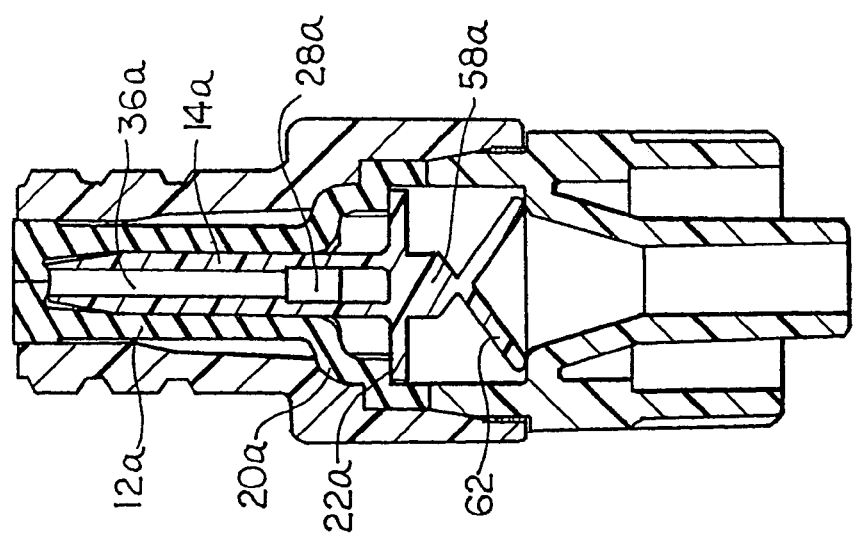
FIG. 10 shows an alternative embodiment of the invention in the closed position.

FIG. 10 shows an alternative valve design, wherein the cannula's outlet end 58a includes a leaf spring 62 to urge the cannula 14a up into its closed position. Like the valve shown in FIG. 1, a widened area of the cannula's outlet end 58a in the FIG. 10 valve forms a second seal area 22a, and a diverter channel 28a redirects flow from the cannula's main passageway 36a. Unlike the FIG. 1 valve, the attachment section 20a of the gland 12a in the FIG. 10 valve is not stretched, but rather it folds upon itself. FIG. 11 shows a variation of the FIG. 10 valve. The FIG. 11 valve is shown in the open position. As shown in FIG. 1, the gland's attachment section 20a is folded as the valve is opened. In the FIG. 11 embodiment, the cannula's outlet end 22b is shaped so as to prevent further movement of the cannula towards the valve's outlet 50 while still permitting flow to the outlet.

Figure 12:
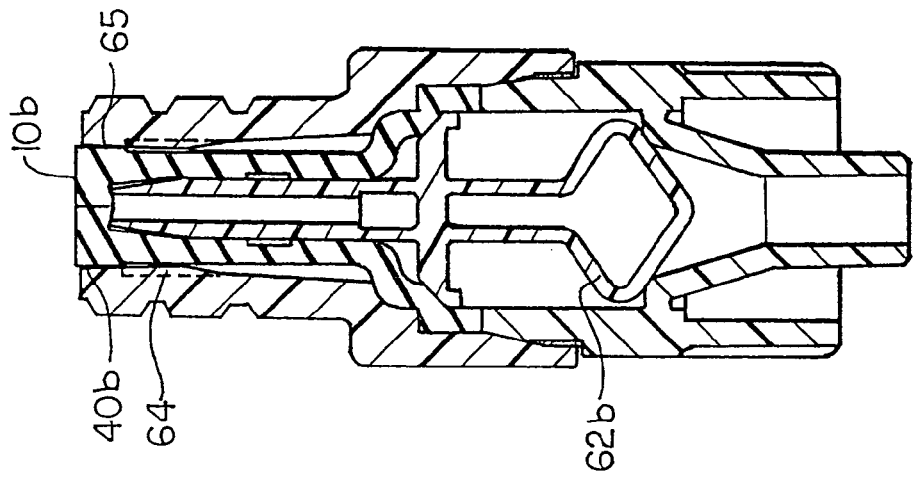
FIG. 12 shows a another alternative embodiment of the invention.

FIG. 12 shows a variation of the FIG. 11 valve with a different variation of the leaf spring 62a. In the FIG. 12 valve, a portion of the tapered zone 40b of the valve's inlet has ribs 64, while another portion 65 of the tapered zone 40b has a frusto-conical shape that is able to maintain contact around the entire circumference of the nozzle. The frusto-conical portion 65 maintains a seal between the nozzle and the valve housing when the nozzle is inserted all the way into the valve. The ribs 64 reduce the friction between the gland's seal section 10b and the tapered zone, so as to make it easier for the seal section 10b to return to its closed position when the nozzle is removed from the valve. The ribs 64 also provide a stronger hold on an inserted nozzle than if the entire tapered zone 40b had frusto-conical shape. The ribs provide a further benefit if a vent is not provided in the inlet housing portion: the ribs reduce the length that the gland has to travel without the space between the gland and the inlet housing portion being vented to atmosphere.

Figure 13A:
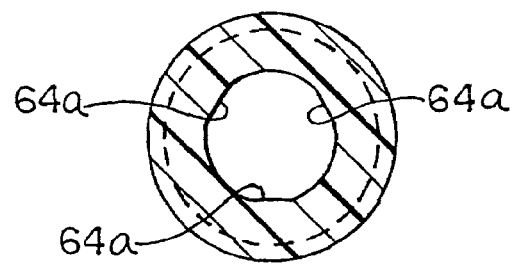
FIG. 13A shows a cross section of the FIG. 13 embodiment.
Figure 13:
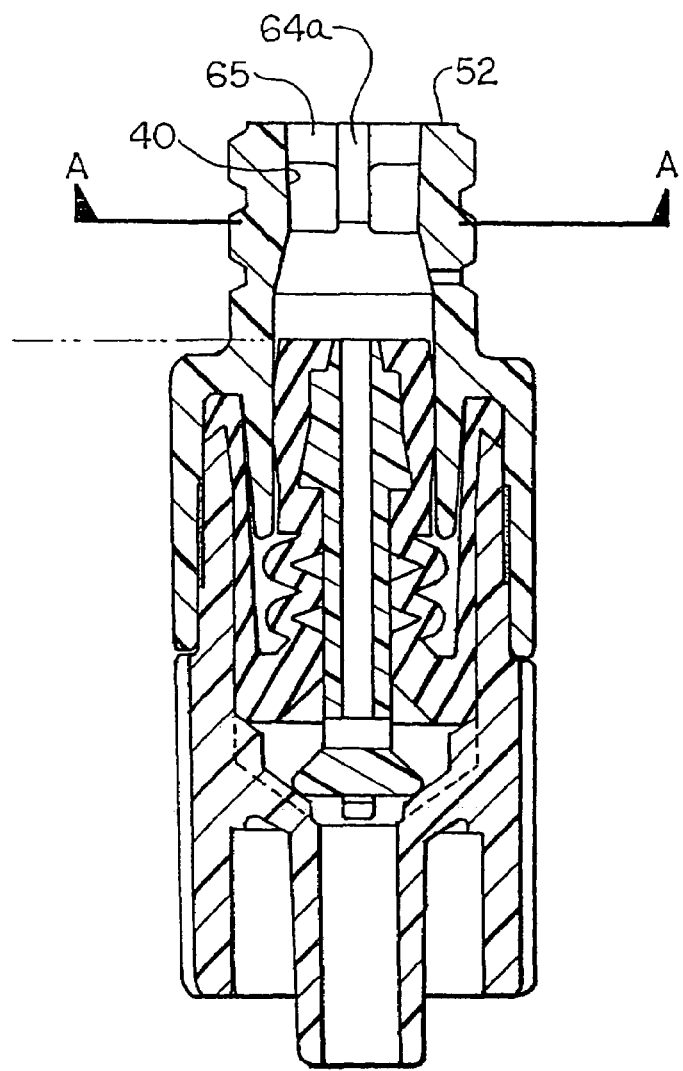
FIG. 13 shows a variation of the FIG. 1 embodiment.

FIG. 13 shows the valve of FIG. 1 adapted to include ribs 64a in the tapered zone 40 of the inlet section. These ribs 64a may also be seen in FIG. 13A, which shows a cross section through the inlet section 40 of the FIG. 13 valve. FIG. 13 also shows the tapered sections of the housing passageway that enable the cannula to properly return from the fully open position to the closed position. Specifically, the passageway may be considered to include three tapered sections (among other sections). The first section begins at the aperture compression zone 40 and converges toward a point "X." In preferred embodiments, the aperture compression zone 40 has an inner diameter of about 0.169 inches and converges toward point X, which has an inner diameter of about 0.162 inches. The second section begins at point X and diverges toward a point "Y" which, in preferred embodiments, may have an inner diameter of about 0.167 inches. The third section begins at point Y and diverges to a point "Z" which, in preferred embodiments, may having an inner diameter of about 0.200 inches.

Figure 14A:
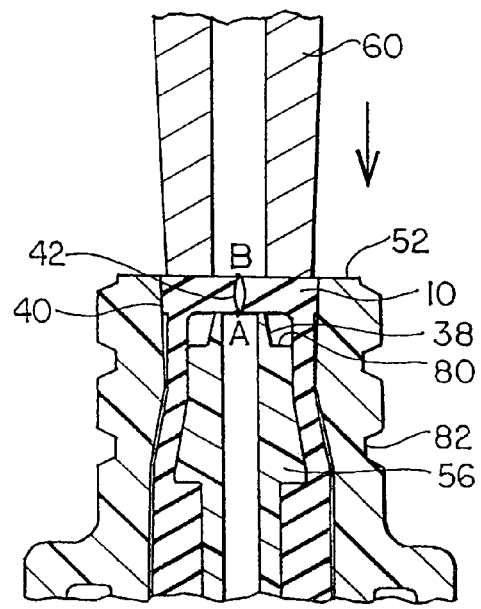
FIGS. 14A-14C shows how the gland's seal section opens in response to a nozzle being inserted into the valve.
Figure 14B:
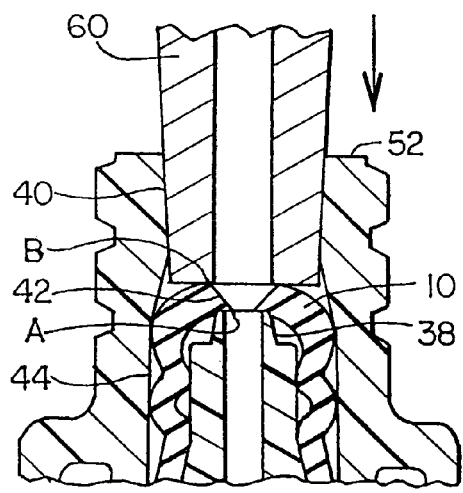
Figure 14C:
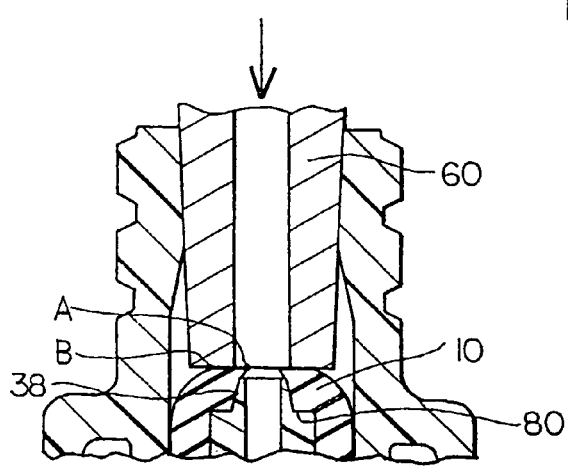

FIGS. 14A-14C show how the seal section 10 of the gland may respond to the insertion of a nozzle 60 into the valve. When the valve is in the closed position, as shown in FIG. 14A, the aperture 42 is closed with both the bottom, point A, and the top, point B, of the aperture being pressed together by the tapered zone of the housing 40. (The exterior of the housing's inlet section preferably includes threads 82 to accept luer-lock threads surrounding a nozzle.) The nozzle 60 pushes the gland's seal section away from the exterior inlet face 52 and the tapered section 40 of the inlet. When the seal section reaches the widened portion 44 of the inlet section, the aperture 42 opens, with the point B of the aperture spreading more than point A, as shown in FIG. 14B. The shaping of the cannula's inlet end allows the aperture 42 to be opened quickly and closed quickly. As the nozzle 60 is inserted further into the valve, as shown in FIG. 14C, the seal section 10 of the gland is prevented from being forced too far down the cannula by step 80 on the cannula. Preferably, a portion of the gland remains between the cannula's inlet end 38 and the nozzle 60. The tip of the cannula's inlet end is preferably rounded (bullet-nosed) to minimize cutting of the gland material between the cannula and the nozzle and to promote the centering of the cannula's inlet end 38 with respect to the nozzle.

Figure 15:
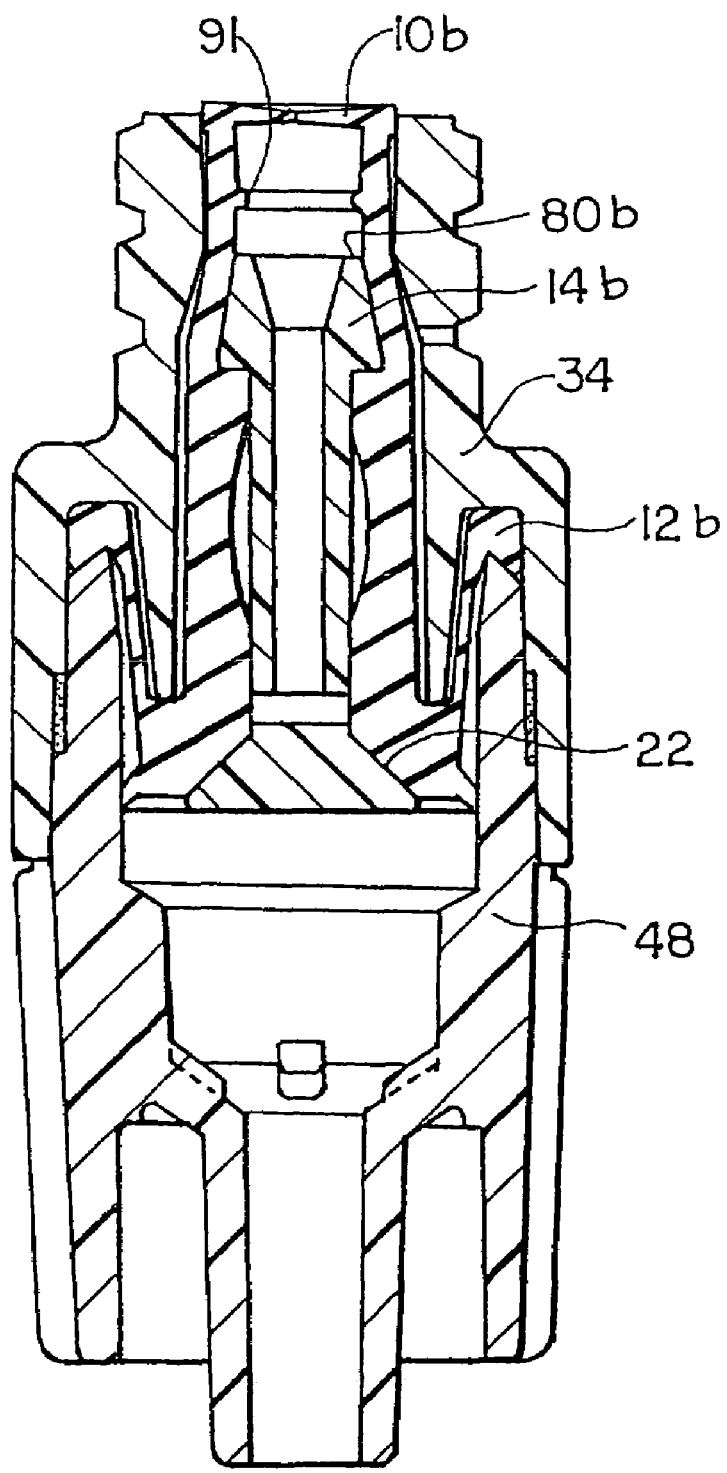
FIG. 15 shows a longitudinal sectional view of a valve according to another embodiment of the invention.

FIG. 15 shows an alternative embodiment of the invention. This embodiment is similar to the FIG. 1 embodiment, as the FIG. 15 embodiment includes a movable center cannula 14b, located inside a gland 12b, which in turn is located within the passageway formed by the inlet housing portion 34 and the outlet housing portion 48. When the valve is in the closed position, the gland's seal section 10b is spaced away from the top end 80b of the cannula 14b. When the valve is being opened, as shown in FIGS. 16A-16D, the gland's seal section 10b moves towards the cannula's top surface 80b. This movement is limited by a step 91 on the inner surface of the gland 14b, which prevents the seal section 10b from moving past cannula's top surface 80b.

Figure 16E:
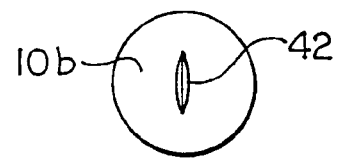
FIGS. 16E-16G show end views of the seal section of FIGS. 16D-16D respectively.
Figure 16A:
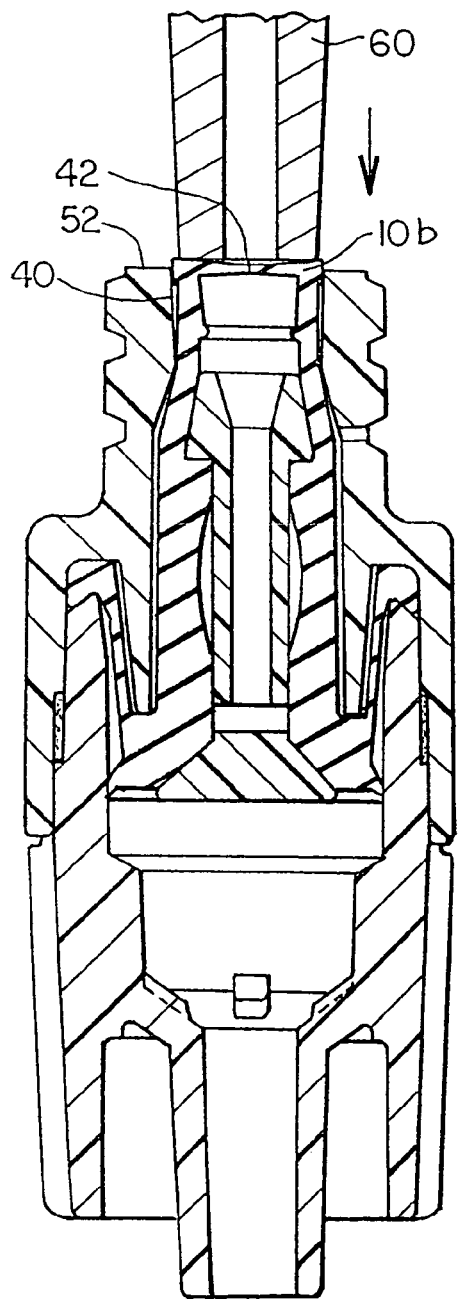
FIGS. 16A-16D show longitudinal sectional views of the valve shown in FIG. 15, as the valve is urged by a luer-taper nozzle from a fully closed position to a fully open position.

As shown in FIG. 16A, the seal section 10b is substantially aligned with the exterior inlet face 52 and extends slightly beyond the exterior inlet face, so as to provide a swabbable surface. The outer diameter of the seal section 10b is a little greater than the inner diameter of the inlet's tapered section 40, so that the resulting pressure keeps the aperture 42 closed when the valve is in the closed position. Because the valve includes a high-pressure seal area 22, the seal section's aperture 42 does not have to resist high back pressure.

Figure 16B:
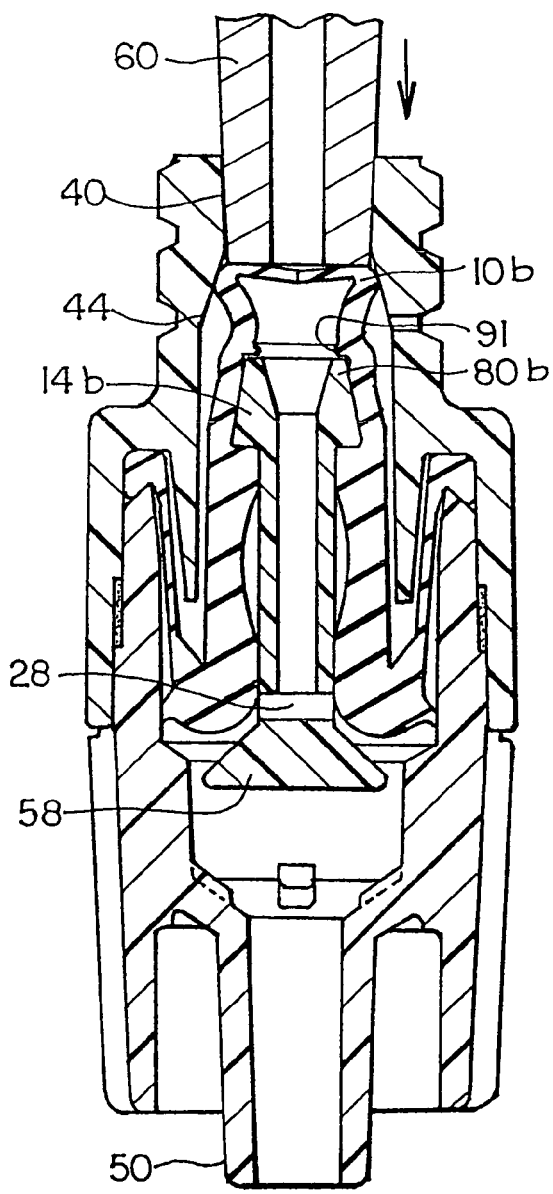

As the nozzle 60 is inserted into the valve's inlet, as shown in FIG. 16B, the gland's seal section 10b is urged towards the cannula 14b, which in turn is urged towards the valve's outlet 50. As the seal section 10 moves from the inlet's tapered section 40 to the inlet's expanding section 44, which has a greater inner diameter than the seal section's outer diameter, the aperture 42 in the gland's seal section 10 begins to open, as can be seen in FIG. 16E. Also, the cannula's outlet end 58 begins to separate from the gland 12b, opening the high-pressure seal and providing fluid communication between the cannula's transverse passage 28 and the valve's outlet 50.

Figure 16F:
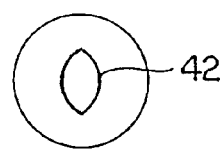
Figure 16G:
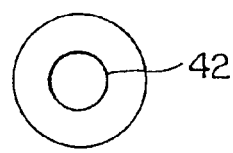
Figure 16C:
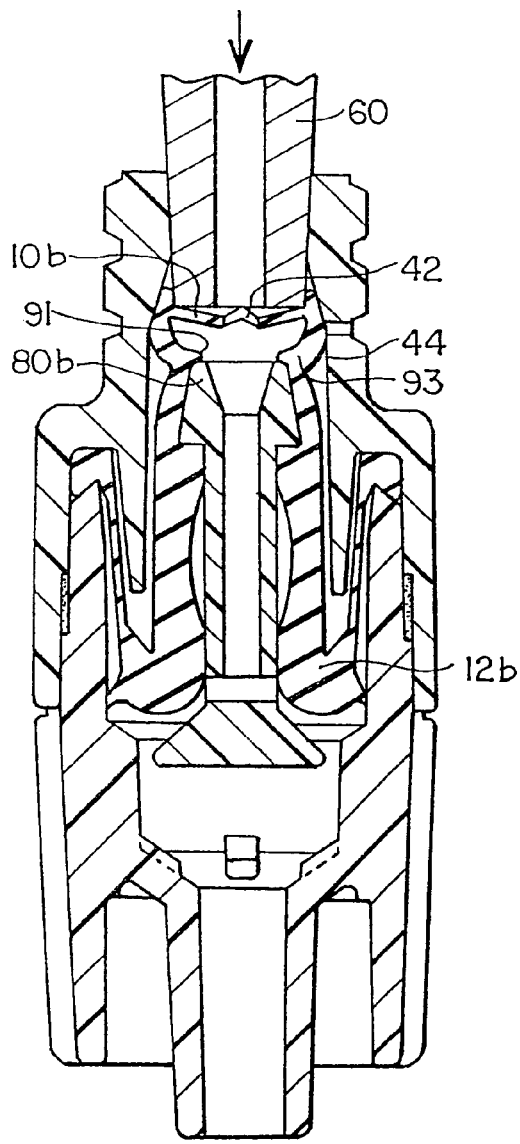

As the nozzle 60 is further inserted into the valve's inlet, as shown in FIG. 16C, the seal section 10b moves further in the inlet's expanding section 44, so that the increasing inner diameter of the inlet permits the seal section's aperture 42 to open further, as shown in FIG. 16F. The step 91 on the inner surface of the gland 14b is pressed against the top surface 80b of the cannula 14b, so that further movement of the seal section 10b towards the cannula 14b causes deformation of the sidewalls 93 of the gland 12b adjacent the seal section 10b.

Figure 16D:
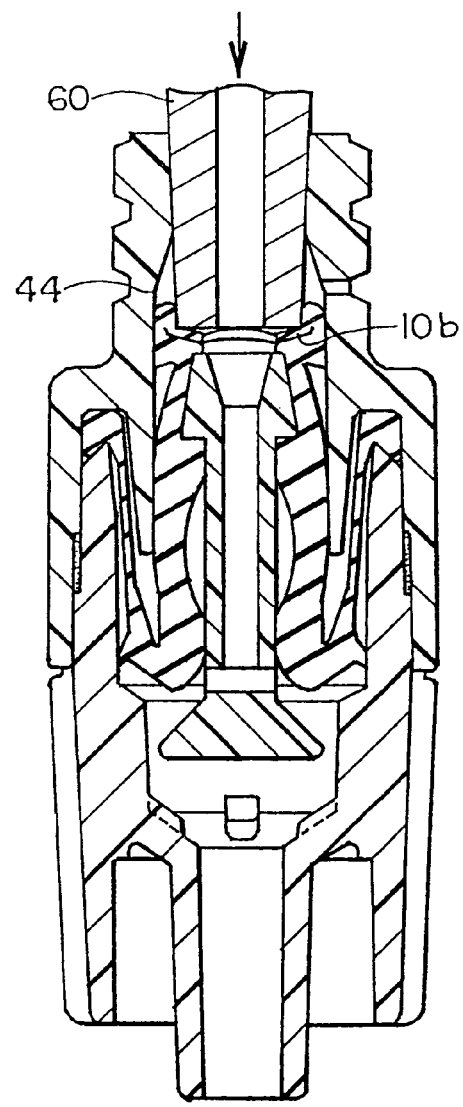

The cannula's top surface 80b, along with the gland's inner lip 91, prevents the seal section 10b from being pushed beyond the cannula's top surface, as shown in FIG. 16D. FIG. 16D shows the nozzle 60 fully inserted into the valve. The seal section's aperture 42 is fully opened, as shown in FIG. 16G. By keeping the seal section 10b from being pushed beyond the cannula's top surface 80b, the seal section 10b is able to spring back to its original position quickly, when the nozzle is removed from the valve.

Figure 17:
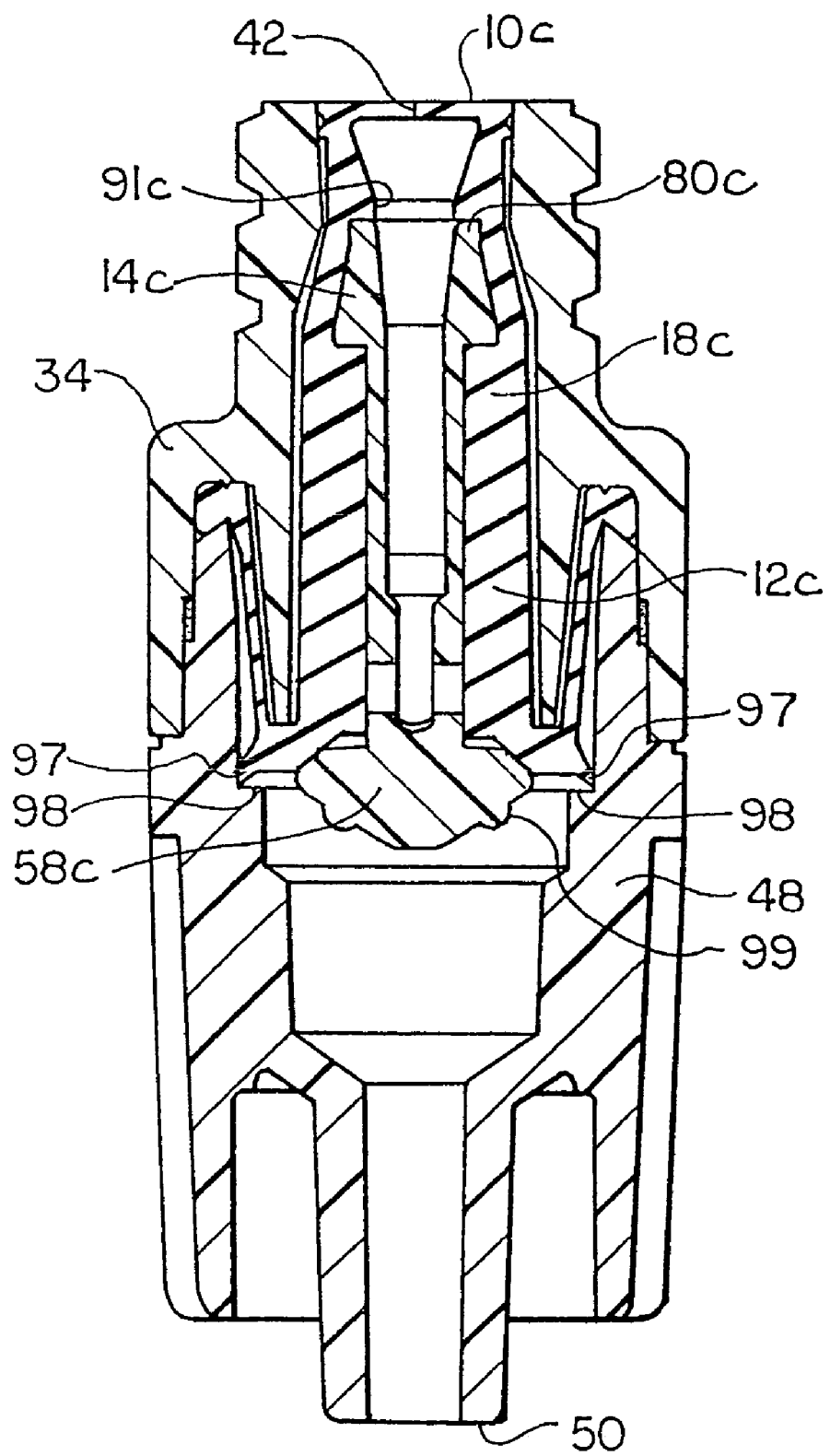
FIG. 17 shows a longitudinal sectional view of a valve according to another embodiment of the invention.

FIG. 17 shows another alternative embodiment of the invention. This embodiment is similar to the embodiment shown in FIG. 15 since it includes a movable center cannula 14c, located inside a gland 12c, which in turn is located within the passageway formed by the inlet housing portion 34 and the outlet housing portion 48. When the valve is in the closed position, the gland's seal section 10c is spaced away from the top end 80c of the cannula 14c. When the valve is being opened, as shown in FIGS. 18A-18D, the gland's seal section 10c moves towards the cannula's top surface 80c. This movement is limited by a step 91c on the inner surface of the gland 12c, which prevents the seal section 10c from moving past cannula's top surface 80c.

Improving upon the embodiment shown in FIG. 15, the gland 12c of FIG. 17 includes a ridge 97 that normally is seated on a ledge 98 formed by the interior walls of the outlet housing portion 48. In addition, the tapered outlet end 58c of the cannula 14c includes ribs 99 for limiting longitudinal motion of the cannula 14c toward the outlet end 50 of the valve. Accordingly, there is no need for ribs to protrude from the interior walls of the outlet housing portion 48.

FIGS. 18A-18D show of the valve of FIG. 17 as it is urged by a luer-taper nozzle 60 from a substantially fully closed position to a substantially fully open position. Specifically, in FIG. 18A, the seal section 10c is substantially aligned with the exterior inlet face 52 and extends slightly beyond the exterior inlet face to provide a swabbable surface. The outer diameter of the seal section 10c is a little greater than the inner diameter of the inlet's tapered section 40, so that the resulting pressure keeps the aperture 42 closed when the valve is in the closed position. Because the valve includes the high-pressure seal area 22, the seal aperture 42 does not have to resist high back pressure.

Figure 18A:
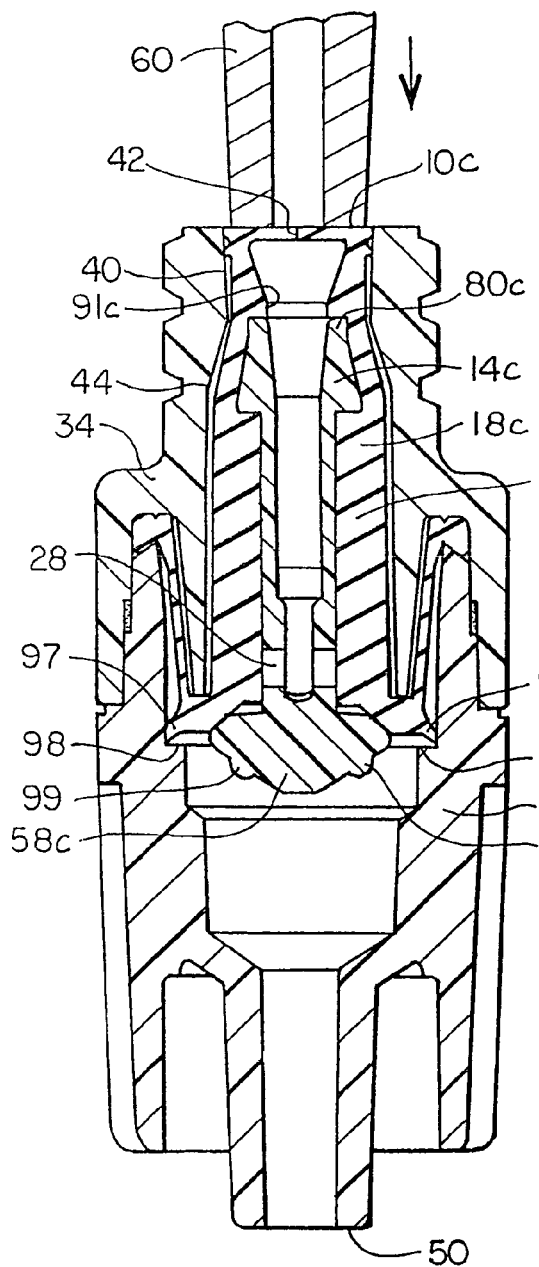
FIGS. 18A-18D show longitudinal sectional views of the valve shown in FIG. 17, as the valve is urged by a luer-taper nozzle from a substantially fully closed position to a substantially fully open position.
Figure 18B:
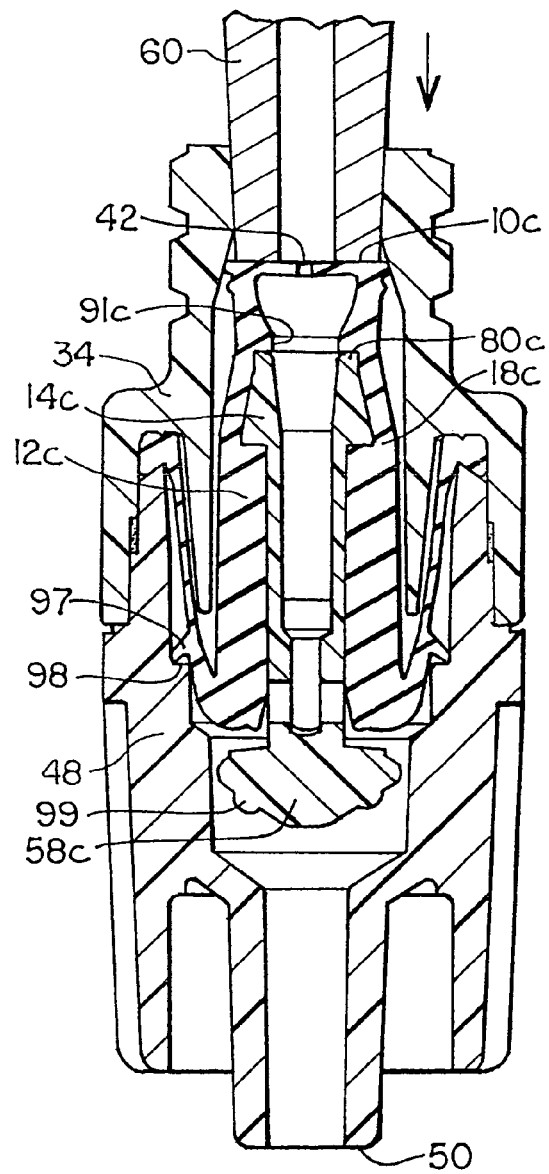

As the nozzle 60 is inserted into the valve's inlet, as shown in FIG. 18B, the gland's seal section 10c is urged towards the cannula 14c, which in turn is urged towards the valve's outlet 50. As the seal section 10c moves from the inlet's tapered section 40 to the inlet's expanding section 44, which has a greater inner diameter than the seal section's outer diameter, the aperture 42 in the gland's seal section 10c begins to open. Also, the cannula's outlet end 58c begins to separate from the gland 12c, opening the high-pressure seal and providing fluid communication between the cannula's transverse passage 28 and the valve's outlet 50.

Figure 18C:
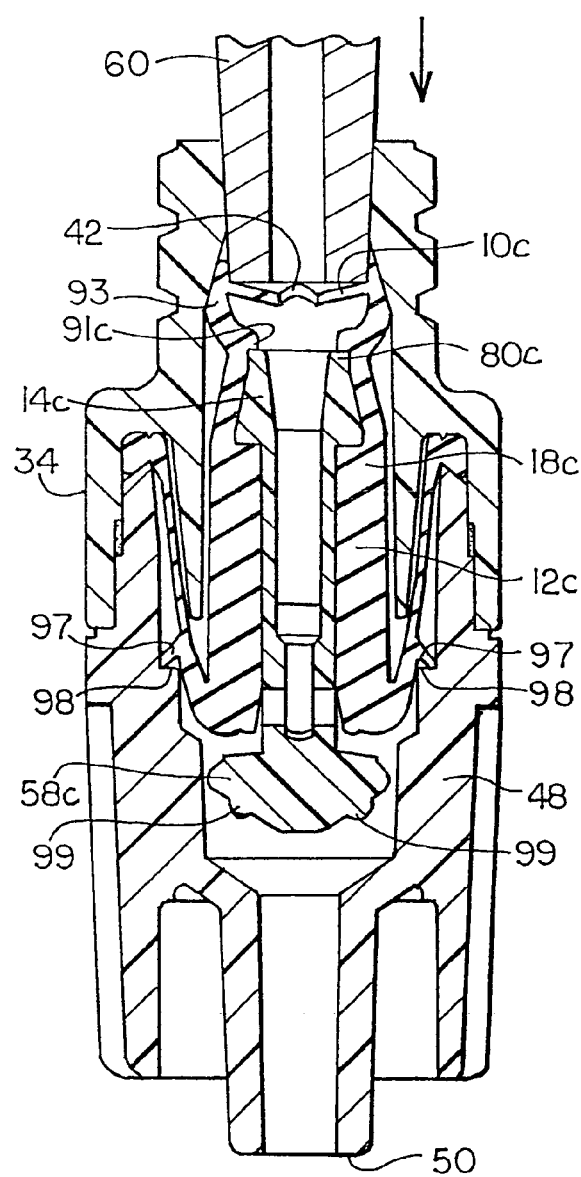

As the nozzle 60 is further inserted into the valve's inlet, as shown in FIG. 18C, the seal section 10c moves further in the inlet's expanding section 44, so that the increasing inner diameter of the inlet permits the seal section's aperture 42 to open further. The step 91c on the inner surface of the gland 12c is pressed against the top surface 80c of the cannula 14c, so that further movement of the seal section 10c towards the cannula 14c causes deformation of the sidewalls 93 of the gland 12c adjacent the seal section 10c.

Figure 18D:
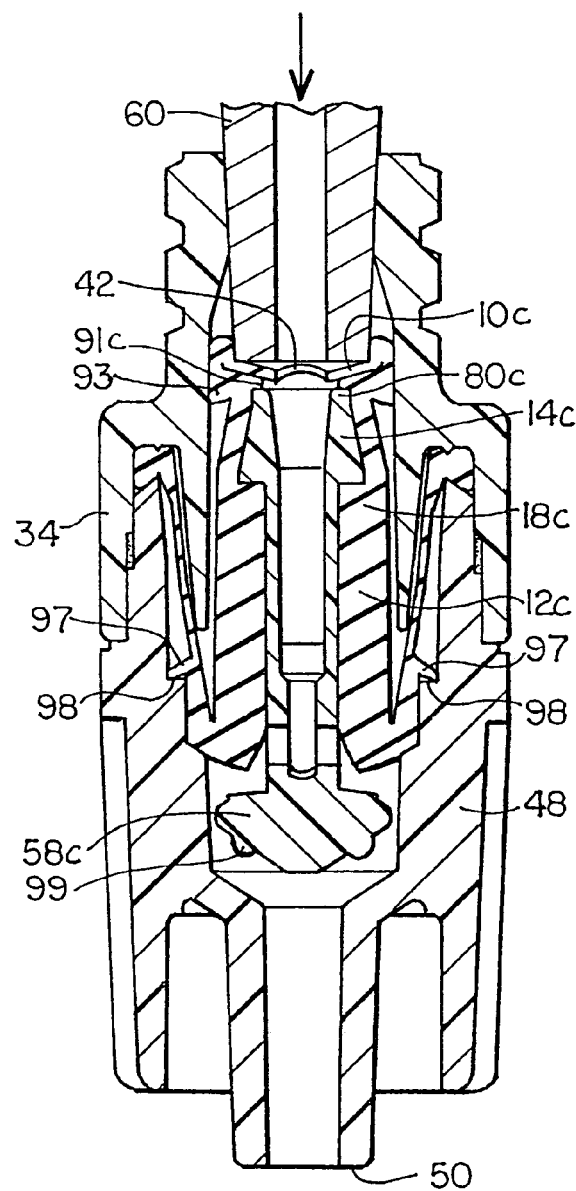

The cannula's top surface 80c, along with the gland's step 91c, prevents the seal section 10c from being pushed beyond the cannula's top surface 80c, as shown in FIG. 18D. FIG. 18D shows the nozzle 60 fully inserted into the valve with the seal section's aperture 42 fully opened. By keeping the seal section 10c from being pushed beyond the cannula's top surface 80c, the seal section 10c is able to spring back to its original position quickly, when the nozzle is removed from the valve. Moreover, the ribs 99 on the outlet end 58c of the cannula 14c limit further longitudinal movement of the cannula 14c toward the outlet 50. It should be noted that the ridge 97 remains seated on the ledge 98 throughout the entire process shown in FIGS. 18A-18D.

Although the invention has been described with reference to several preferred embodiments, it will be understood by one of ordinary skill in the art that various modifications can be made without departing from the spirit and the scope of the invention, as set forth in the claims hereinbelow.

We claim:

1. A medical valve comprising:
   a housing defining a passageway, the passageway having an inlet section and an outlet section;
   a plug member movably mounted within the passageway, the plug member being a cannula and defining a channel for directing fluid through the valve; and a substantially flexible, resilient gland member secured to the housing and the plug member, the plug member being supported within the passageway by the gland member, wherein the plug member is substantially rigid, wherein the plug member has a proximal end, a distal end, and a distal section, the plug member having an opening nearer to its distal end, the gland member normally occluding the opening and contacting the distal section of the plug member, the distal section being the portion of the plug member distal to the opening.

2. The valve as defined by claim 1 wherein the plug member is movable between a closed mode that prevents fluid flow through the valve, and an open mode that permits fluid flow through the valve.

3. The valve as defined by claim 2 wherein the plug member prevents fluid flow through the valve when the valve is in the closed mode.

4. The valve as defined by claim 2 wherein the plug member occludes the passageway when the valve is in the closed mode.

5. The valve as defined by claim 2 wherein the plug member provides at least a portion of an unoccluded fluid path through the valve when the valve is in the open mode.

6. The valve as defined by claim 1 wherein the gland has a seal section, further wherein the inlet section of the housing has an exterior inlet face, the seal section being substantially aligned with the exterior inlet face when the valve is closed to provide a swabbable surface.

7. The valve as defined by claim 1 wherein the plug member has a longitudinal axis that is substantially parallel with the direction of motion of the plug member.

8. The valve as defined by claim 1 wherein the plug member is at least partially within the gland member.

9. The valve as defined by claim 1 wherein the plug member is formed from a plug material, the gland member being formed from a gland material, the plug material being different from the gland material.

10. The valve as defined by claim 1 wherein the housing comprises an inlet housing and an outlet housing, the gland member being secured between the inlet housing and the outlet housing.

11. The valve as defined by claim 1 wherein the resilient gland member is attached to the housing and the plug member.

12. The valve as defined by claim 1, wherein a portion of the resilient gland member circumscribes at least a portion of the plug member.

13. The valve as defined by claim 1, wherein the opening allows fluid flow through the plug member when the valve is in an open mode.

14. A medical valve comprising:
a housing defining a passageway, the passageway having an inlet section and an outlet section;
a plug member movably mounted within the passageway, the plug member defining a channel for directing fluid through the valve; and
a substantially flexible, resilient gland member secured to the housing and the plug member, the plug member being supported within the passageway by the gland member,
wherein the plug member is substantially rigid,
wherein the plug member has a proximal end, a distal end, and a distal section, the plug member having an opening nearer to its distal end, the gland member normally occluding the opening and contacting the distal section of the plug member, the distal section of the plug member being the portion of the plug member distal to the opening.

15. The valve as defined by claim 14 wherein the plug member is movable between a closed mode that prevents fluid flow through the valve, and an open mode that permits fluid flow through the valve.

16. The valve as defined by claim 15 wherein the plug member prevents fluid flow through the valve when the valve is in the closed mode.

17. The valve as defined by claim 15 wherein the plug member occludes the passageway when the valve is in the closed mode.

18. The valve as defined by claim 15 wherein the plug member provides at least a portion of an unoccluded fluid path through the valve when the valve is in the open mode.

19. The valve as defined by claim 14 wherein the gland has a seal section, further wherein the inlet section of the housing has an exterior inlet face, the seal section being substantially aligned with the exterior inlet face when the valve is closed to provide a swabbable surface.

20. The valve as defined by claim 14 wherein the plug member has a longitudinal axis that is substantially parallel with the direction of motion of the plug member.

21. The valve as defined by claim 14 wherein the plug member is at least partially within the gland member.

22. The valve as defined by claim 14 wherein the plug member is formed from a plug material, the gland member being formed from a gland material, the plug material being different from the gland material.

23. The valve as defined by claim 14 wherein the housing comprises an inlet housing and an outlet housing, the gland member being secured between the inlet housing and the outlet housing.

24. A medical valve comprising:
a housing defining a passageway, the passageway having an inlet section and an outlet section;
a plug member movably mounted within the passageway, the plug member being a cannula, wherein the plug member is movable between a closed mode that prevents fluid flow through the valve, and an open mode that permits fluid flow through the valve, the plug member providing at least a portion of an unoccluded fluid path through the valve when the valve is in the open mode; and
a substantially flexible, resilient gland member secured to the housing and the plug member, the plug member being supported within the passageway by the gland member,
wherein the plug member is substantially rigid, wherein the plug member has a proximal end, a distal end, and a distal section, the plug member having an opening nearer to its distal end, the gland member normally occluding the opening and contacting the distal section of the plug member, the distal section of the plug member being the portion of the plug member distal to the opening.

25. The valve as defined by claim 24 wherein the plug member defines a channel for directing fluid through the valve.

26. The valve as defined by claim 24 wherein the plug member prevents fluid flow through the valve when the valve is in the closed mode.

27. The valve as defined by claim 24 wherein the plug member occludes the passageway when the valve is in the closed mode.

28. The valve as defined by claim 24 wherein the gland has a seal section, further wherein the inlet section of the housing has an exterior inlet face, the seal section being substantially aligned with the exterior inlet face when the valve is closed to provide a swabbable surface.

29. The valve as defined by claim 24 wherein the plug member has a longitudinal axis that is substantially parallel with the direction of motion of the plug member.

30. The valve as defined by claim 24 wherein the plug member is at least partially within the gland member.

31. The valve as defined by claim 24 wherein the plug member is formed from a plug material, the gland member being formed from a gland material, the plug material being different from the gland material.

32. The valve as defined by claim 24 wherein the housing comprises an inlet housing and an outlet housing, the gland member being secured between the inlet housing and the outlet housing.

33. A medical valve comprising:
   a housing defining a passageway, the passageway having an inlet section and an outlet section;
   a plug member movably mounted within the passageway, wherein the plug member is movable between a closed mode that prevents fluid flow through the valve, and an open mode that permits fluid flow through the valve, the plug member providing at least a portion of an unoccluded fluid path through the valve when the valve is in the open mode; and
   a substantially flexible, resilient gland member secured to the housing and the plug member, the plug member being supported within the passageway by the gland member,
   wherein the plug member is substantially rigid,
   wherein the plug member has a proximal end, a distal end, and a distal section, the plug member having an opening nearer to its distal end, the gland member normally occluding the opening and contacting the distal section of the plug member, the distal section of the plug member being the portion of the plug member distal to the opening.

34. The valve as defined by claim 33 wherein the plug member defines a channel for directing fluid through the valve.

35. The valve as defined by claim 33 wherein the plug member prevents fluid flow through the valve when the valve is in the closed mode.

36. The valve as defined by claim 33 wherein the plug member occludes the passageway when the valve is in the closed mode.

37. The valve as defined by claim 33 wherein the gland has a seal section, further wherein the inlet section of the housing has an exterior inlet face, the seal section being substantially aligned with the exterior inlet face when the valve is closed to provide a swabbable surface.

38. The valve as defined by claim 33 wherein the plug member has a longitudinal axis that is substantially parallel with the direction of motion of the plug member.

39. The valve as defined by claim 33 wherein the plug member is at least partially within the gland member.

40. The valve as defined by claim 33 wherein the plug member is formed from a plug material, the gland member being formed from a gland material, the plug material being different from the gland material.

41. The valve as defined by claim 33 wherein the housing comprises an inlet housing and an outlet housing, the gland member being secured between the inlet housing and the outlet housing.

* * * * *

UNITED STATES PATENT AND TRADEMARK OFFICE
CERTIFICATE OF CORRECTION

| | | |
|---|---|---|
| PATENT NO. | : 7,789,864 B2 | Page 1 of 1 |
| APPLICATION NO. | : 10/700344 | |
| DATED | : September 7, 2010 | |
| INVENTOR(S) | : Cote, Sr. et al. | |

It is certified that error appears in the above-identified patent and that said Letters Patent is hereby corrected as shown below:

In Col. 9, line 23
replace "unoceluded"
with "unoccluded."

Signed and Sealed this
Twenty-eighth Day of June, 2011

David J. Kappos
*Director of the United States Patent and Trademark Office*